United States Patent [19]

Miller et al.

[11] 4,160,767

[45] Jul. 10, 1979

[54] VINCA ALKALOID INTERMEDIATES

[75] Inventors: Jean C. Miller; Gerald E. Gutowski, both of Indianapolis, Ind.

[73] Assignee: Eli Lilly and Company, Indianapolis, Ind.

[21] Appl. No.: 935,431

[22] Filed: Aug. 21, 1978

Related U.S. Application Data

[62] Division of Ser. No. 869,546, Jan. 16, 1978, abandoned, which is a division of Ser. No. 747,575, Dec. 6, 1976, Pat. No. 4,096,148.

[51] Int. Cl.$^2$ .......................................... C07D 519/04
[52] U.S. Cl. ................................................ 260/244.4
[58] Field of Search ....................... 546/51; 260/244.4

[56] References Cited

U.S. PATENT DOCUMENTS

| | | | |
|---|---|---|---|
| 3,944,554 | 3/1976 | Tafur | 260/244.4 |
| 4,029,663 | 6/1977 | Gutowski et al. | 260/244.4 |

*Primary Examiner*—Donald G. Daus
*Assistant Examiner*—David E. Wheeler
*Attorney, Agent, or Firm*—James L. Rowe; Arthur R. Whale

[57] ABSTRACT

3-Spiro-5''-oxazolidine-2'',4''-dione derivatives of Vinca alkaloids, useful as anti-tumor agents and as intermediates.

1 Claim, No Drawings

VINCA ALKALOID INTERMEDIATES

This is a division of application Ser. No. 869,546, filed Jan. 16, 1978 now abandoned which was in turn a division of then copending application Ser. No. 747,575 filed Dec. 6, 1976, now U.S. Pat. No. 4,096,148 issued June 20, 1978,

BACKGROUND OF THE INVENTION

Several naturally-occurring alkaloids obtainable from *Vinca rosea* have been found active in the treatment of experimental malignancies in animals. Among these are leurosine (U.S. Pat. No. 3,370,057), vincaleukoblastine (vinblastine) to be referred to hereinafter as VLB (U.S. Pat. No. 3,097,137), leuroformine (Belgian Pat. No. 811,110); leurosidine (vinrosidine) and leurocristine (to be referred to hereafter as vincristine) (both in U.S. Pat. No. 3,205,220); deoxy VLB "A" and "B", *Tetrahedron Letters*, 783 (1958); 4-desacetoxyvinblastine (U.S. Pat. No. 3,954,773; 4-desacetoxy-3'-hydroxyvinblastine (U.S. Pat. No. 3,944,554); leurocolombine (U.S. Pat. No. 3,890,325) and vincadioline (U.S. Pat. No. 3,887,565). Two of these alkaloids, VLB and vincristine, are now marketed as drugs for the treatment of malignancies, particularly the leukemias and related diseases in humans. Of these marketed compounds, vincristine is a most active and useful agent in the treatment of leukemias but is also the least abundant of the anti-neoplastic alkaloids of *Vinca rosea*. The two marketed alkaloids are customarily administered by the i.v. route.

Chemical modification of the Vinca alkaloids has been rather limited. In the first place, the molecular structures involved are extremely complex, and chemical reactions which effect a specific functional group of the molecule without changing other groups are difficult to develop. Secondly, alkaloids lacking desirable chemotherapeutic properties have been recovered or produced from *Vinca rosea* fractions or alkaloids, and a determination of their structures has led to the conclusion that these compounds are closely related to the active alkaloids. Thus, anti-neoplastic activity seems to be limited to very specific structures, and the chances of obtaining more active drugs by modification of these structures would seem to be correspondingly slight. Among the successful modifications of physiologically-active alkaloids has been the preparation of dihydro VLB (U.S. Pat. No. 3,352,868) and the replacement of the acetyl group at C-4 (carbon no. 4 of the VLB ring system—see the numbered structure below) with higher alkanoyl group or with unrelated acyl groups. (See U.S. Pat. No. 3,392,173.) Several of these derivatives are capable of prolonging the life of mice inoculated with P1534 leukemia. One of the derivatives in which a chloracetyl group replaced the C-4 acetyl group of VLB was also a useful intermediate for the preparation of structurally modified VLB compounds in which an N,N-dialkylglycyl group replaced the C-4 acetyl group of VLB (See U.S. Pat. No. 3,387,001). C-3 carboxamide derivatives of VLB, vincristine, vincadioline etc. have also been prepared and found to be active anti-tumor agents. (Belgian Pat. No. 813,168) These compounds are extremely interesting because, for example, the 3-carboxamides of VLB are more active against Ridgeway osteogenic sarcoma and Gardner lymphosarcoma than is VLB itself from which they are derived. Certain of the amide derivatives actually approach the activity of vincristine against these tumors. One of these amides, 4-desacetyl VLB C-3 carboxamide or vindesine, is currently on clinical trial in humans and has been found active in certain leukemias. In humans, vindesine appears to have less neurotoxicity than does vincristine.

SUMMARY OF THE INVENTION

This invention provides compounds represented by Formula I below:

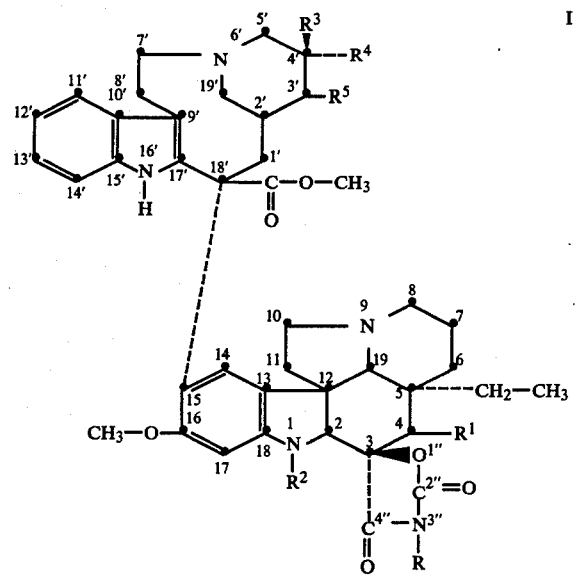

wherein R is H, $C_1$-$C_4$ alkyl, $C_3$-$C_4$ alkenyl, $CH_2$—CHX—$CH_3$ or $CH_2$—$CH_2X$;
wherein X is Br or Cl;

$R^1$ is OH, O—C(=O)—$CH_3$ or O—C(=O)—NH—R;

$R^2$ is H, $CH_3$ or CHO;
one of $R^3$ and $R^4$, when taken singly, is H or OH and the other $C_2H_5$;
$R^5$, when taken singly, is H;
and $R^4$ and $R^5$, when taken together, form an epoxide; and pharmaceutically-acceptable salts thereof.

In the above formula the term "$C_1$-$C_4$ alkyl" includes such alkyl groups as methyl, ethyl, n-propyl, isobutyl, n-butyl, isopropyl, sec-butyl, and t-butyl, and the term "$C_3$-$C_4$ alkenyl" includes allyl, methallyl, and crotyl.

Compounds of the above formula can be described generically as derivatives of VLB where $R^1$ is acetoxy, $R^2$ is methyl, $R^3$ is hydroxyl, $R^4$ is ethyl and $R^5$ is H, of vincristine where $R^1$ is acetoxy, $R^2$ is formyl, $R^3$ is hydroxyl, $R^4$ is ethyl and $R^5$ is H, as derivatives of desmethyl VLB (also known as desformylvincristine) where $R^1$ is acetoxy, $R^2$ is hydrogen, $R^3$ and $R^4$ are hydroxyl and ethyl, respectively, and $R^5$, is H, of leurosidine where $R^1$ is acetoxy, $R^2$ is methyl, $R^3$ is ethyl, $R^4$ is hydroxyl and $R^5$ is H, of Deoxy VLB "A", where $R^1$ is acetoxy, $R^2$ is methyl, $R^3$ and $R^5$ are H and $R^4$ is ethyl; of Deoxy VLB "B" wherein $R^1$, $R^2$ and $R^5$ are the same as in Deoxy VLB "A" but $R^3$ is ethyl and $R^4$ is hydrogen, of leurosine wherein $R^1$ is acetoxy, $R^2$ is methyl, $R^3$ is ethyl and $R^4$ and $R^5$ taken together form an α-epoxide ring or of leuroformine, the corresponding compound in which $R^2$=CHO. The compounds of this invention have been named as 3-spiro-5"-oxazolidinedione derivatives of the particular alkaloid listed above; for example, an oxazolidinedione derived from VLB would be named as 3-descarbomethoxy-3-deshydroxy VLB 3-spiro-5″-oxazolidine-2″,4″-dione. According to the above name, a spiro compound is formed in which the spiro carbon atom is carbon 3 of the vinca alkaloid ring system and carbon 5″ of the oxazolidinedione ring system. In naming the compounds of this invention systematically, the terms "3-descarbomethoxy-3-deshydroxy" have been used to indicate that the carbomethoxy group and the hydroxy group at 3 have been replaced by (or incorporated into) the oxazolidine ring. In order to simplify the naming of the compounds of this invention, however, the term "3-descarbomethoxy-3-deshydroxy" will be omitted since the presence of the oxazolidine ring in each of the compounds will be understood to have replaced the hydroxy and carbomethoxy groups at carbon 3 in the vinca alkaloid. It will be understood, therefore, that each name herein of an oxazolidinedione will implicitly contain the terms "3-descarbomethoxy-3-deshydroxy".

Non-toxic acids useful for forming pharmaceutically-acceptable acid addition salts of the compounds of this invention include salts derived from inorganic acids such as: hydrochloric acid, nitric acid, phosphoric acid, sulfuric acid, hydrobromic acid, hydriodic acid, nitrous acid, phosphorus acid and the like, as well as salts of non-toxic organic acids including aliphatic mono and dicarboxylates, phenyl-substituted alkanoates, hydroxy alkanoates and alkandioates, aromatic acids, aliphatic and aromatic sulfonic acids, etc. Such pharmaceutically-acceptable salts thus include the sulfate, pyrosulfate, visulfate, sulfite, bisulfite, nitrate, phosphate, monohydrogenphosphate, dihydrogenphosphate, metaphosphate, pyrophosphate, chloride, bromide, iodide, acetate, propionate, decanoate, capyrylate, acrylate, formate, isobutyrate, caprate, heptoanate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonates, toluenesulfonate, chlorobenzenesulfonate, xylenesulfonate, phenylacetate, phenylpropionate, phenylbutyrate, citrate, lactate, 2-hydroxybutyrate, glycollate, malate, tartrate, methanesulfonate, propanesulfonate, naphthalene-1-sulfonate, naphthalene-2-sulfonate and the like salts.

The compounds of this invention are prepared according to the following reaction scheme.

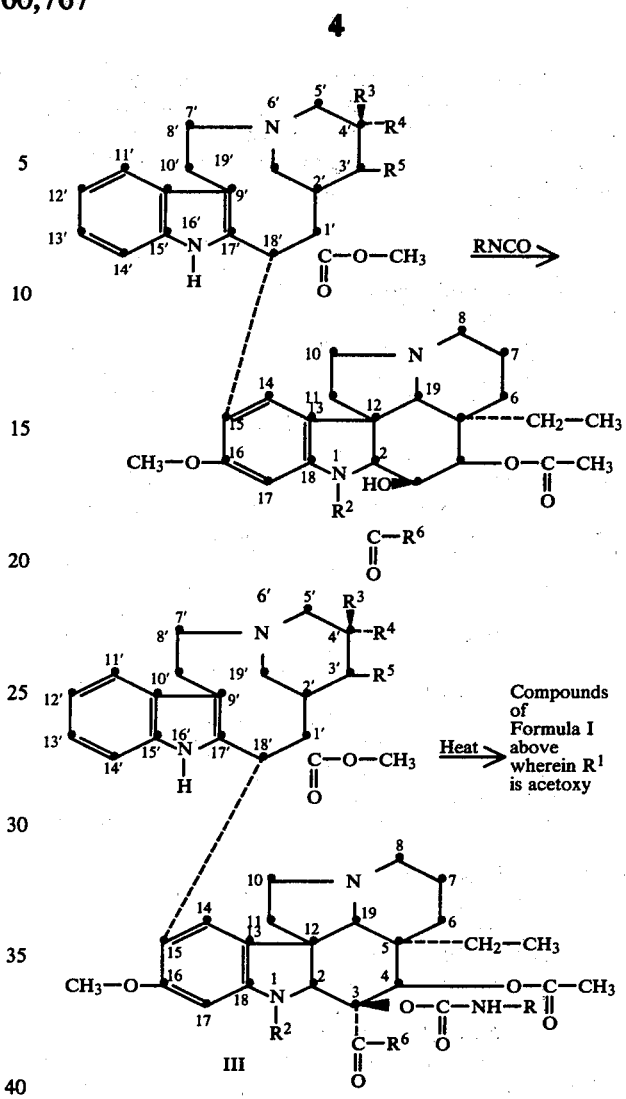

wherein R, $R^2$, $R^3$, $R^4$ and $R^5$ have the same meanings as hereinabove and $R^6$ is $OCH_3$ or $NH_2$.

In the above reaction scheme, a dimeric indoledihydroindole alkaloid having an acetoxy group at C-4, either obtained by extraction of the leaves of *Vinca rosea* or prepared semi-synthetically by chemical modification of such dimeric compounds or by coupling two monomeric indoles, dinhdroindoles etc., is reacted with an isocyanate-RNCO- to yield an intermediate 3-carbamate represented by formula III. These carbamates are relatively unstable at ordinary reaction temperatures such as 40°-100° C. and rearrange to the spirooxazolidinediones of this invention, represented by formula I above. The stability of the 3-carbamate group depends to a large degree upon the nature of the R-substituent on the carbamate nitrogen. For example, when R is β-chloroethyl, the intermediates 3-carbamate compound can be isolated from the reaction of excess isocyanate and the dimeric alkaloid (II) by chromatography and can be rearranged to a spirooxazolidinedione (I) with heat. 3-Carbamates formed with methylisocyanate, rearrange to the spirooxazolidinedione under standard reaction conditions. The 3-carbamates can be isolated by carrying out the reaction at a relatively low temperature. The compound is isolated soon after the isocyanate has been added in most instances rather than subject it to heating for prolonged periods. The isolated intermediate 3-carbamate is rearranged to a spirooxazolidinedione (III) by heating at 40°-100° C. for several hours.

The 3-carbamates of formula III are not only useful as intermediates in the synthesis of the compounds of formula I, but also have anti-tumor activity of their own as evidenced by their ability to inhibit the growth of transplanted tumors in mice.

A second type of intermediate is frequently isolated from the reaction of an isocyanate and dimeric indole-dihydroindole alkaloid of Formula II, particularly where an excess of isocyanate is employed and benzene is the solvent. This intermediate is a water-soluble precipitate comprising a complex of the vinca alkaloid and, presumably, more than one molecule of isocyanate per molecule of alkaloid. If, for example, an excess of $\beta$-chloroethylisocyanate is reacted with VLB, the subsequent water-soluble complex forms a precipitate which is isolated by filtration. A solution of the filtered complex in water produces the 3"-($\beta$-chloroethyl)spirooxazolidinedione after standing at room temperature for 16 hours. Other isocyanates behave in similar fashion with VLB and other dimeric vinca alkaloids but only certain of the complexes (depending apparently on the nature of the R group of the isocyanate, RNCO) are isolatable at ordinary reaction temperatures.

In carrying out the above Reaction Scheme without isolation of the intermediate carbamate (III), the vinca alkaloid (II) as the free base is dissolved in an inert organic solvent such as benzene and the desired isocyanate (RNCO), usually in excess, is added thereto. The reaction mixture is refluxed until oxazolidinedione formation is substantially complete and is then cooled. Removal of the solvent and excess isocyanate by evaporation yields the oxazolidinedione as a residue which can be further purified as by chromatography. Other inert solvents which can be used in the above reaction include methylene dichloride, chloroform, toluene and the like.

Compounds according to formula I in which R is H are preferably prepared by the following alternate procedure. Vindesine is reacted with sodium hydride in the presence of dimethylcarbonate. The product of this reaction has an unsubstituted spirooxazolidinedione ring but also has an hydroxy in place of an acetoxy group at C-4 ($R^1$=OH). Reaction of this compound with 1 mole of acetic anhydride under mild reaction conditions yields a compound according to formula I above wherein R is H and $R^1$ is acetoxy.

If a 4-desacetyl alkaloid such as 4-desacetyl VLB or 4-desacetyl vincristine is employed as a starting material, the product of the isocyanate reaction is a 3-spiro-5"-oxazolidine-2",4"-dione-4-carbamate (O—CO—NHR). These 4-carbamate oxazolidinedione derivatives are also active anti-tumor agents as well as intermediates for the preparation of compounds in which $R^1$ is OH or, ultimately, acetoxy.

Compounds according to I above in which $R^1$ is OH are prepared by acidic hydrolysis of compounds according to I above in which $R^1$ is acetoxy. These compounds in which $R^1$ is OH can be reacted with an isocyanate (RNCO) to yield compounds in which $R^1$ is

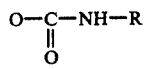

by simple reaction in an inert solvent, preferably with gentle heating. These 4-carbamates are also prepared by utilizing as a starting material in the above reaction scheme a compound in which $R^1$ is OH.

Pharmaceutically-acceptable acid addition salts of the 3-spiro-5"-oxazolidine-2",4"-dione derivatives of those vinca alkaloids as represented by formula I above are prepared by mixing a solution of the alkaloidal free base with 1 mole of the desired non-toxic acid in an inert solvent. If the salt is soluble, it is recovered by evaporation of the solvent in vacuo. If the salt is insoluble in the reaction medium, it will precipitate and be collected by filtration. Certain of the inorganic salts are prepared by a somewhat different procedure. For example, the sulfate salt is prepared by dissolving a free base according to formula I above in a minimal amount of a polar organic solvent such as ethanol and then adjusting the pH of this solution to about 4.0 by the dropwise addition of 2% aqueous sulfuric acid in ethanol. The sulfate salt is recovered by evaporation of the solvents to dryness. The hydrochloride salt can be prepared in similar fashion by adding an alcoholic solution of HCl to an alcoholic solution of the free base. The acid addition salts prepared as above can be purified by such well-known techniques such as chromatography or recrystallization.

As previously mentioned, the compounds of this invention are also useful as intermediates for the preparation of other anti-tumor vinca alkaloids. Treatment of the oxazolidinedione (I) with base yields a C-3 carboxamide derivative usually lacking the acetyl group at C-4. For example, reaction of VLB 3"-methyl-3-spiro-5"-oxazolidine-2",4"-dione woth aqueous alkali yields 4-desacetyl VLB C-3 N-methylcarboxamide. The C-3 carboxamide derivatives of the vinca alkaloid such as VLB, vincristine, leurosidine, and deoxy VLB "A" and "B" are active anti-tumor agents in animals as set forth in the copending application of Cullinan and Gerzon Ser. No. 721,650, filed Sept. 8, 1976. The C-3 amides of leurosine and of leuroformine, which alkaloids are included in the scope of formula II above, are also active anti-tumor agents against transplanted tumors in experimental animals.

Certain of the compounds represented by formula I above, those in which R is $CH_2CH_2X$ or $CH_2CHXCH_3$, are useful intermediate in a different reaction scheme. It has been found that reaction of, for example, VLB 3"-($\beta$-chloroethyl) 3-spiro-5"-oxazolidine-2",4"-dione with sodium hydrosulfide yields the N-($\beta$-mercaptoethyl) derivative as an intermediate which is not isolated but is concurrently hydrolyzed to yield the C-3 N-($\beta$-mercaptoethyl)carboxamide of 4-desacetyl VLB, a highly effective anti-tumor agent in mice. The previous procedure for the preparation of this compound involved the conversion of VLB into 4-desacetyl VLB C-3 hydrazide which was in turn reacted with nitrous acid to yield the corresponding azide. The azide was then reacted with $\beta$-mercaptoethylamide under basic conditions to yield the desired C-3 carboxamide. The yield in this latter 3-step procedure is not as satisfactory nor is the handling of the materials as easy as with the above 2-step process utilizing the oxazolidinedione as an intermediate. Other nucleophilic reagents can react with the 3"-($\beta$-chloroethyl)spirooxazolidinedione to yield the correspondingly substituted spirooxazolidinedione, which compound can in turn be transformed to the C-4 hydroxy C-3 carboxamide.

The starting materials according to formula II above are either isolated from the leaves of the plant vinca rosea such as VLB, vincristine, leurosidine, leurosine, leuroformine, deoxy VLB "A" and "B", or, when $R^6$ in II is $NH_2$, prepared by reacting the corresponding compound in which $R^6$ is $OCH_3$ with hydrazine to yield a 4-desacetyl C-3 hydrazide which can be hydrogenylysed with Raney nickel to yield the corresponding 4-desacetyl 3-carboxamide. The 4-desacetyl compound can be reacetylated if desired at C-4 by the procedure of Hargrove, *Lloydia*, 27, 340 (1964) or by acetylation under mild conditions using 1 mole of acetic anhydride. Starting materials represented by formula II when $R^2$ is H or formyl, except for vincristine, N-desformyl leurocristine, N-desformylleuroformine and leuroformine, all of which are obtained from leaves of *Vinca rosea*, are prepared as follows. The 1-methyl group of Deoxy VLB "A" or "B", etc. (in fact, any compound represented by II in which $R^2$ is methyl and $R^6$ is methoxy) can be oxidized with chromium oxide in glacial acetic acid at $-60°$ C. to yield a mixture of compounds in which $R^2$ is H or formyl, according to the procedure set forth in U.S. Pat. No. 3,899,493. The compounds in which $R^2$ is H can be formylated or compounds in which $R^2$ is formyl can be deformylated.

This invention is further illustrated by the following specific examples.

EXAMPLE 1

PREPARATION OF VLB 3"-METHYL-3-SPIRO-5"-OXAZOLIDINE-2",4"-DIONE

A solution was prepared containing 2.84 g. of VLB free base in 40 ml. of anhydrous benzene. 15 ml. of methylisocyanate were added thereto and the resulting mixture heated to refluxing temperature for about 6 hours. The reaction mixture was cooled and the volatile constituents removed by evaporation. The residue comprising VLB 3"-methyl-3-spiro-5"-oxazolidine-2",4"-dione formed in the above reaction was purified by chromatography over 200 g. of silica (activity I). The chromatogram was developed with 1 liter of 4% methanol in benzene followed by 2.5 liters of 6% methanol in benzene which eluted VLB 2"-methyl-3-spiro-5"-oxazolidine-2",4"-dione; weight=0.9764 g.; molecular ion at 835; nmr δ at 0.17, 0.88, 2.0, 2.60, 2.74, 2.78, 2.81, 3.08 (new $NCH_3$) 3.58, 3.60, 3.79, 4.52, 5.18, 5.41, 5.88, 6.09, 6.64; mass spectrum ions at 849 (trans-methylation), 835, 817, 804, 776, 650, 543, 494, 355, 167, 154, 149, 135.

Other 3"-substituted oxazolidinediones preparable by the above procedure include VLB 3"-n-butyl-3-spiro-5"-oxazolidine-2",4"-dione. Mass spectrum ions at 891, 877 859, 837, 836, 819, 818, 792, 747, 650, 543, 536, (512), 381, 380, 355, 341, 325, 295, (188), 154, 149, 135 and 6, 122, 121, 107. Nmr in deuterochloroform, δ at 0.66, 0.92, 1.3–1.7, 1.99, 2.07, 2.81, 3.61, 3.79, 5.17, 5.43, 5.87, 6.09, 6.61.

VLB 3"-allyl-3-spiro-5"-oxazolidine-2",4"-dione. Mass spectrum; ions at 875, 861, 843 and 4, 830 and 1, 802 and 3, (784), 650, 543, 520, 380 and 1, 355, 295, 273, 242, 154, 149, 143, 136, 135 122, 121, 107. Infrared spectrum in chloroform; peaks at 3440, 1810, 1740, 1610 cm$^{-1}$. Nmr, δ at 0.66, 0.88, 1.98, 2.41, 2.80, 3.57, 3.60, 3.79, 4.14, 5.1–5.3, 5.43, 5.7–5.95, 6.08, 6.63.

EXAMPLE 2

PREPARATION OF VINCRISTINE 3"-METHYL-3-SPIRO-5"-OXAZOLIDINE-2",4"-DIONE

Vincristine free base obtained from 158.3 mg. of vincristine sulfate by standard procedures was dissolved in about 15 ml. of anhydrous benzene. About 2.5 ml. of methylisocyanate were added to the vincristine solution and the resulting mixture was heated to refluxing temperature for about 6 hours and then kept at ambient temperature overnight, followed by an additional 4 hour reflux. The volatile constituents were removed leaving a residue weighing 159.6 mg. which was soluble in methanol but not soluble in methylene dichloride. Preparative thin-layer chromatography yielded 4 bands of which the third, in order of polarity, was vincristine 3"-methyl-3-spiro-5"-oxazolidone-2",4"-dione, having the following physical characteristics. Mass spectrum; ions at 863, 849, 831, 818, 806, 790, 751, 708, 647, 650, 635, 480, 393, 369, 355, 283, 270, 268, 183, 171, 168, 154, 141, 136, 122, 121. Infrared spectrum in chloroform; peaks at 3440, 1805, 1730, (and 1745), 1660 cm$^{-1}$. Nmr in deuterochloroform; δ at 0.59, 0.88, 1.35, 1.68, 2.74, 2.78, 3.01, 3.65, 3.87, 4.41, 4.68, 5.20, 5.90, 6.81, 6.91, 8.12, 8.78.

EXAMPLE 3

PREPARATION OF 1-DESMETHYL-4-DESACETYL-4-(N-METHYL-CARBAMOYLOXY) VLB 3"-METHYL-3-SPIRO-5"-OXAZOLIDINE-2",4"-DIONE

Following the procedure of Example 1, 21.7 mg. of 1-desmethyl-4-desacetyl VLB were reacted with 3 ml. of methylisocyanate in about 12 ml. of anhydrous methylene dichloride. 1-Desmethyl-4-desacetyl-4-(N-methylcarbamoyloxy) VLB 3"-methyl-3-spiro-5"-oxazolidine-2",4"-dione formed in the above reacted was isolated by the procedure of Example 1 and purified by preparative thin-layer chromatography. The compound had the following physical characteristics. Nmr (in deuterochloroform); δ at 2.75, 2.79, 3.08, 3.59, 3.76, 3.84, 4.76, 5.35, 5.19, 5.86, 6.26, 6.68. Infrared spectrum in chloroform showed a new peak at 1818 cm.$^{-1}$, and increased absorption at 1740 cm$^{-1}$ and at 1130 cm$^{-1}$ compared with starting material. Molecular spectrum; ions at 836, 834, 779, 777, 368, 256, 241, 213, 155, and 149.

EXAMPLE 4

PREPARATION OF VLB 3"-(β-CHLOROETHYL)-3-SPIRO-5"-OXAZOLIDINE-2",4"-DIONE

Following the procedure of Example 1, VLB was reacted with β-chloroethylisocyanate in 100 ml. of anhydrous benzene. The reaction mixture was stirred for 16 hours at room temperature followed by 2 hours heating at reflux temperature. A precipitate comprising a water-soluble complex of VLB and β-chloroethylisocyanate separated and was recovered from the cooled solution by filtration. The precipitate was dissolved in about 30 ml. of water and the aqueous solution stirred at room temperature for about 16 hours. The solution was then made basic by the addition of dilute sodium hydroxide and VLB 3"-(β-chloroethyl)-3-spiro- 5"-oxazolidine-2",4"-dione, formed in the above reaction, being insoluble in basic solution, separated and was extracted into methylene dichloride. The methylene dichloride extracts were combined and the solvent removed therefrom by evaporation. The residue comprising VLB 3"-(β-chloroethyl)-3-spiro-5"-oxazolidine-2",4"-dione was purified by chromatography over 150 g. of silica (activity I). The chromatogram was developed with 6% methanol in benzene. The compound had the following physical characteristics; molecular spectrum; ion peaks at 883, 847, 816, 789, 650, 592, 591, 543, 506, 485, 451, 355, 295, 154, 136, 135, 122, 121, 107. Infrared spectrum (in chloroform) peaks at 3650, 3570, 3440, 1805, 1745, 1610 cm$^{-1}$. Nmr in deuterochloroform, δ at 0.67, 0.88, 2.01, 2.81, 285, 3.61, 3.79, 3.87, 5.19, 5.44, 5.89, 6.11, and 6.65.

EXAMPLE 5

ALTERNATE PREPARATION OF VLB 3"-(β-CHLOROETHYL)-3-SPIRO-5"-OXAZOLIDINE-2",4"-DIONE AND OF VLB 3-N-(β-CHLOROETHYL)CARBAMATE

A solution was prepared containing 481.2 mg. of VLB free base in 14 ml. of anhydrous benzene. 7.0 ml. of β-chlorethylisocyanate were added thereto. There was an immediate precipitate. The reaction mixture was heated at refluxing temperature for about 16 hours. The benzene was removed by evaporation in vacuo and the residue subjected to preparative thin-layer chromatography over silica using a 3:1 ethyl acetate-methanol solvent system. Two inseparable mobile bands were isolated together (with a total yield of 379.4 mg.) and rechromatographed. A second chromatography using the same 3:1 ethyl acetate-methanol solvent system with only 47 mg. of the 2 component mixture per preparative plate resulted in a separation into VLB 3"-(β-chloroethyl)-3-spiro-5"-oxazolidine-2",4"-dione (147 mg.) and VLB 3-N-(β-chloroethyl)carbamate. This latter compound had the following physical characteristics; mass spectrum; ion peaks at (881), 835, 821, 790, 763, 692, 591, 543, 480, 409, 353, 295, 293, 283, 281, 278, 243, 188, 154, 149, 135. Infrared spectrum in chloroform showed maxima at 3645, 3575, 3450, 3405 (new) 1730, 1675 (new), 1610 cm$^{-1}$. Nmr in deuterochloroform; δ at 0.88, 0.80, 1.35, 2.05, 2.76, 2.80, 3.60, 3.77, 5.32, 5.53, 5.84, 6.09, 6.60, 10.0 (broad).

EXAMPLE 6

PREPARATION OF 4-DESACETYL VLB 3"-METHYL-3-SPIRO-5"-OXAZOLIDONE-2",4"-DIONE

About 100 mg. of VLB 3"-methyl-3-spiro-5"-oxazolidine-2",4"-dione were refluxed in 0.5 N aqueous hydrochloric acid for about 1.5 hours. The aqueous solution was made basic and 4-desacetyl VLB 3"-methyl-3-spiro-5"-oxazolidone-2",4"-dione, being insoluble in base; separated and was extracted into methylene dichloride. The methylene dichloride extracts were combined and the solvents evaporated therefrom in vacuo. The residue was subjected to preparative thin-layer chromatography over silica gel using a 3:1 ethyl acetate-methanol solvent mixture to develop the chromatogram. The main band comprised 4-desacetyl VLB 3"-methyl-3-spiro-5"-oxazolidone-2",4"-dione. The compound was single spot material in three other chromatographic systems. It had the following physical characteristics: molecular ion spectrum; ion peaks at 807, 793, 763, 762, 749, 734, 690, 493; 452, 408, 355, 295, 268, 167, 171, 154, 149, 143, 135, 122, 121, 107. Infrared spectrum in chloroform, maxima at 3580, 3440, 1815, 1735, 1615 cm$^{-1}$. Nmr in deuterochloroform; δ at 0.80, 0.88, 2.70, 2.81, 2.90, 3.04, 3.59, 3.76, 3.92, 4.20, 5.60, 5.88,

EXAMPLE 7

PREPARATION OF VLB 3-SPIRO-5"-OXAZOLIDINE-2",4"-DIONE

A suspension of 208.0 mg. of sodium hydride (as a 50% oil dispersion) was prepared in 20 ml. of tetrahydrofuran. 200.9 mg. of vindesine (VLB C-3 carboxamide) were added thereto. After the solution had been stirred at ambient temperature for 25 minutes. 4.0 ml. of dimethylcarbonate were added. The reaction mixture was then stirred at ambient temperature for 4.5 hours after which time the volatile constituents were removed by evaporation. Water was added and the aqueous solution acidified with dilute hydrochloric acid. The acidic layer was extracted three times with methylene dichloride and the methylene dichloride extracts were discarded. The aqueous layer was then made basic with 10% percent aqueous sodium hydroxide. VLB 3-spiro-5"-oxazolidine-2",4"-dione, being insoluble in the basic layer separated and was extracted with 4 portions of methylene dichloride. The methylene dichloride extracts were combined and the solvent removed by evaporation. The residue weighing 98.4 mg. was subjected to preparative thin-layer chromatography over silica using a 1:1 ethyl acetate-methanol solvent system. 4 bands were seen, the fourth band comprising 4-desacetyl VLB 3-spiro-5"-oxazolidone-2",4"-dione. The band was separated mechanically and eluted from the silica. Evaporation of the eluting solvent yielded a residue weighing 10.9 mg. with the following physical characteristics. Nmr in deutereochloroform; δ at 0.90, 2.87, 3.57, 3.65, 3.84, 3.95, 5.5–6.0, 6.08, 8.5. Infrared spectrum, maxima at 3680, 3470, 1810, 1735, 1620, 1505, 1460, 1435, 1335, 1010, 910 cm$^{-1}$. Molecular spectrum; ions at 807, 793, 763, 749, 718, 706, 692, 690, 634, 434, 422, 408, 355, 351, 325, 323, 297, 295, 269, 268, 187, 167, 154, 149, and 135. Field desorption molecular ions; 779, 753, 735.

Oxazolidinediones lacking a substituent on the ring nitrogen can exist in tautomeric forms in which the hydrogen on the ring nitrogen can enolize with either of the carbonyl groups present in the ring to form an hydroxy oxazolinone. More specifically, an oxazolidine-2,4-dione can tautomerize to either a 2-hydroxy-2-oxazoline-4-one or a 4-hydroxy-3-oxazoline-2-one. It is believed that the product of the above reaction contains at least two of such tautomeric forms if not all three.

EXAMPLE 8

PREPARATION OF 4-DESACETYL VLB 3"-METHYL-3-SPIRO-5"-OXAZOLIDINE-2",4"-DIONE-4-(N-METHYL)CARBAMATE

A solution was prepared containing 304 mg. of 4-desacetyl VLB in 10 ml. of anhydrous benzene. 5 ml. of methylisocyanate were added thereto and the resulting solution refluxed for about 6 hours. The solvent was removed by evaporation in vacuo to leave a residue weighing 444.4 mg. Thin layer chromatography indicated that 2 materials were present in the residue and these were separated by preparative thin-layer chromatography using a 3:1 ethyl acetate-methanol solvent system. This procedure yielded purified 4-desacetyl VLB 3"-methyl-3-spiro-5"-oxazolidine-2",4"-dione-4-(N-methyl)carbamate having the following physical characteristics: Molecular spectrum; ions at 850, 807, 793, 775, 762, 734, 452, 355, 154, and 135. Ultraviolet spectrum in ethanol; peaks at 215 and 268 with shoulders at 290 and 298 microns. Infrared spectrum (in chloroform); maxima at 3700, 3460, 1816, 1743, 1600 cm$^{-1}$. Nmr in deuterochloroform; δ at 0.67, 0.88, 2.78, 2.81, 3.07, 3.60, 3.70, 5.0, 5.25, 5.30, 5.84, 6.08 and 6.03. This compound showed metaphase arrest activity in a standard mitotic inhibition test at concentrations as low as 10$^{-3}$ mmg/ml.

EXAMPLE 9
PREPARATION OF 4-DESACETYL VLB C-3 N-METHYLCARBOXAMIDE

The following Example illustrates the conversion of the oxazolidinediones of this invention to the C-3 carboxamides of dimeric indole-dihydro indole alkaloids disclosed in Belgian Pat. No. 813168 as well as the C-3 carboxamides of related dimeric Vinca alkaloids, said amides being useful for the same purpose of those disclosed in Belgian Pat. No. 813168.

A solution was prepared from 100 mg. of VLB 3"-methyl-3-spiro-5"-oxazolidine-2",4"-dione in 15 ml. of methanol and 30 ml. of 2 N aqueous sodium hydroxide. The reaction mixture is heated to refluxing temperature for about 15 minutes after which time the methanol was removed by evaporation in vacuo. The aqueous solution was extracted with methylene dichloride. The extracts were combined, the solvents removed therefrom in vacuo, and the resulting residue dried by employing a benzene azeotrope. An 84.4 percent yield (76.3 mg.) of 4-desacetyl VLB C-3-N-methyl-carboxamide was obtained.

EXAMPLE 10
PREPARATION OF SALTS

Salts of the oxazolidinediones (I above) and of the 3-carbamates (III above) are prepared as follows:

The free base is dissolved in a minimal quantity of ethanol. The pH is lowered to 4.0±0.2 by dropwise addition of 2 percent sulfuric acid in ethanol. The pH is determined by taking a 2-drop aliquot, diluting the drop to 1 ml. with water and then determining the pH using a pH meter. The acidic ethanolic solution is evaporated to dryness. The residue comprising the sulfate salt can be recrystallized from methanol or ethanol if desired.

The compounds of this invention have been shown to be active against transplanted tumors in mice in vivo and to induce metaphase arrest in Chinese hamster ovary cells maintained in tissue culture. In demonstrating activity of the drugs of this invention against transplanted tumors in mice, a protocol was used which involved the administration of the drug, usually by the intraperitoneal route, at a given dose level for 7-10 days after innoculation with the tumor.

The following table—Table 1—gives the results of several experiments in which mice bearing transplanted tumors were treated successfully with a compound of this invention. In the table, column 1 gives the name of the compound; column 2, the transplanted tumor; column 3, the dose level or dose level range and the number of days the dosage was administered; column 4, the route of administration, and column 5, the percent inhibition of tumor growth or percent prolongation of survival time, e.g., B16 and P388. (ROS is an abbreviation for Ridgeway osteogenic sarcoma; GLS for Gardner lymphosarcoma; P1534(J) and P388 are leukemias; CA 755 is an adenocarcinoma; and B16 is a melamoma).

TABLE 1

| Compound | Tumor | Dose mg./kg. × days | Route | Percent Inhibition or Prolongation of Survival Time |
|---|---|---|---|---|
| VLB 3"-methyl-3-spiro-5"-oxazolidine-2",4"-dione | | | | |
| free base | GLS | 3-5 × 10 | PO | 37-56% |
| | | 0.6 × 7 | IP | 100% |
| | | 1.25 × 9 | IP | 100% |
| Sulfate salt | B16 | 0.5-0.6 × 10 | IP | 156-8% (3 indefinite |
| | | 4.5 × 10 | IP | 49-91% survivors)* |
| | CA755 | 0.5-1.0 × 10 | IP | 43-100% |
| | P1534 (J) | .5-.6 × 10 | IP | 100% |
| | | 3-4 × 8 | PO | 100% |
| | GLS | 3-4 × 10 | PO | 100% |
| | ROS | 5-7 × 10 | PO | 38-59% |
| 4-(N-methylcarbamoyloxy)-4-desacetyl VLB 3"-methyl-3-spiro-5"-oxazolidine-2",4"-dione | GLS | 0.1-2.5 × 7-9 | IP | 40-100% |
| VLB 3"-(β-chloroethyl)-3-spiro-5"-oxazolidine 2",4"-dione | | | | |
| free base | GLS | 0.5-0.6 × 9-10 | IP | 50-74% |
| | | 3-4 × 9 | PO | 92-100% |
| Sulfate salt | GLS | 0.65 × 10 | IP | 47% |
| | CA755 | 0.75-1.0 × 10 | IP | 53% |
| | | 3-5 × 9-10 | PO | 59-92% |
| | B16 | 0.4-0.6 × 10 | IP | 25-178% (5-indefinite |
| | P1534(J) | 3.5 × 8 | PO | 100% survivors)* |
| | | 0.4-0.6 × 10 | IP | 61-86% |
| 4-Desacetyl VLB 3"-methyl-3-spiro-5"-oxazolidine-2",4"-dione | GLS | 2.5 × 7 | IP | 27% |
| VLB 3"-allyl-3-spiro-5"-oxazolidine-2",4"-dione | GLS | 2.5 × 7 | IP | 35% |
| Vincristine 3"-methyl-3-spiro-5"-oxazolidine- | | | | |

TABLE 1-continued

| Compound | Tumor | Dose mg./kg. × days | Route | Percent Inhibition or Prolongation of Survival Time |
|---|---|---|---|---|
| 2",4"-dione | GLS | 1.0 × 7 | IP | 61% |

* *Survived for 60 days till end of trial.

As seen from the above Table, the oxazolidine diones of this invention are active by the oral route. This oral activity is quite unexpected since the marketed drugs VLB and vincristine do not show this degree of oral activity against the same tumors in experimental animals. For example, VLB 3"-methyl-3-spiro-5"-oxazolidine-2",4"-dione and its 3"-(β-chloroethyl) analogue give 100% inhibitory activity orally against GLS, ROS and CA755 at dose levels of 6-7 and 3-6 mg./kg. whereas VLB and vincristine are only marginally active, if at all, at 2 and 2-4.5 mg./kg. dose levels respectively and usually are toxic at higher levels. Parenterally, however, (via the intraperitoneal route) comparable tumor inhibition or prolongation of life is shown at the 0.5-0.75 mg./kg. dose levels for the oxadolidine diones and at dose levels of 0.4-0.45 mg./kg. for VLB and 0.2-0.25 for vincristine.

In utilizing the novel oxazolidine diones of this invention as anti-tumor agents in mammals, either the parenteral or oral route of administration may be employed. For oral dosage, a suitable quantity of a pharmaceutically-acceptable salt of a base according to formulas I formed with a non-toxic acid is mixed with starch or other excipient and the mixture placed in telescoping gelatin capsules each containing from 7.5-50 mg. of active ingredients. Similarly, a pharmaceutically-acceptable salt can be mixed with starch, a binder, and a lubricant and the mixture compressed into tablets each containing from the 7.5-50 mgs. of salt. The tablets may be scored if lower or divided dosages are to be used. With parenteral administration, the intravenous route is preferred although with smaller mammals such as mice the intraperitoneal route is used. For parenteral administration, isotonic solutions are employed containing 1-10 mg./ml. of a salt of an oxazolidinedione of formula I. The compounds are administered at a rate of from 0.01 to 1 mg./kg. and preferably from 0.1 to 1 mg./kg. of mammalian body weight once or twice a week or every two weeks depending on both the activity and the toxicity of the drug. An alternative method of arriving at a therapeutic dose is based on body-surface area with a dose in the range of 0.1 to 10 mg./meter squared of mammalian body surface every 7 or 14 days.

We claim:
1. A compound of the formula

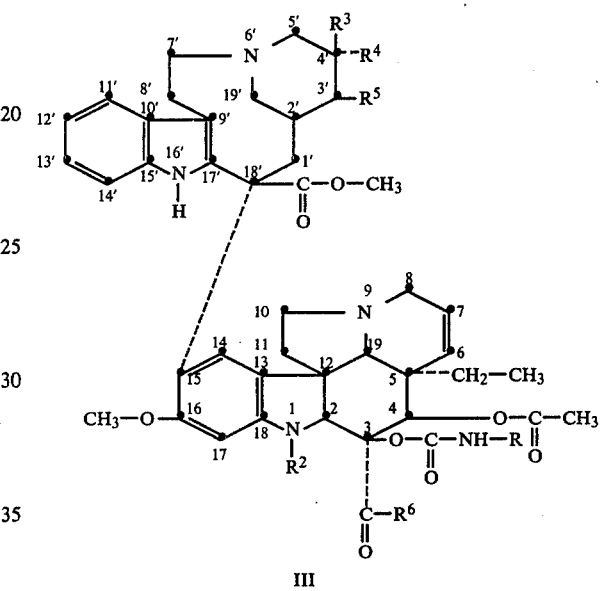

III wherein R is $C_1$-$C_4$ alkyl, $C_3$-$C_4$ alkenyl, $CH_2$—CHX—$CH_3$ or $CH_2$—$CH_2$X wherein X is Cl or Br;
$R^2$ is H, $CH_3$ or CHO;
one of $R^3$ and $R^4$, when taken singly, is H or OH and the the other is ethyl;
$R^5$, when taken singly, is H;
$R^4$ and $R^5$ taken together form an epoxide ring; and
$R^6$ is $OCH_3$ or $NH_2$.

* * * * *